US005601207A

United States Patent [19]

Paczonay

[11] Patent Number: 5,601,207

[45] Date of Patent: Feb. 11, 1997

[54] BITE VALVE HAVING A PLURALITY OF SLITS

[76] Inventor: Joseph R. Paczonay, 3050 Aptos Hill La., Aptos, Calif. 95003

[21] Appl. No.: 615,611

[22] Filed: Mar. 13, 1996

[51] Int. Cl.$^6$ .............................. A61M 31/00; A61F 2/00

[52] U.S. Cl. ........................... 220/703; 215/11.4; 239/33; 251/342

[58] Field of Search .................................... 220/703, 714, 220/715; 215/11.1, 11.4, 388; 251/342; 239/24, 33

[56] References Cited

U.S. PATENT DOCUMENTS

| | | | |
|---|---|---|---|
| 274,447 | 3/1883 | Kennish | 251/342 X |
| 420,651 | 2/1890 | Fowler | 215/11.4 |
| 2,219,604 | 10/1940 | Trotter . | |
| 2,584,359 | 2/1952 | Miles | 215/11.4 |
| 2,943,794 | 7/1960 | Sussman | 239/33 |
| 2,989,961 | 6/1961 | Blanchett | 215/11.4 X |
| 3,822,720 | 7/1974 | Souza . | |
| 4,804,015 | 2/1989 | Albinsson | 251/342 X |
| 4,966,580 | 10/1990 | Turner et al. | 215/11.4 X |
| 4,968,294 | 11/1990 | Salama | 251/342 X |
| 5,085,349 | 2/1992 | Fawcett . | |
| 5,301,860 | 4/1994 | Paczonay . | |

*Primary Examiner*—Steven M. Pollard
*Attorney, Agent, or Firm*—Thomas R. Lampe

[57] ABSTRACT

A bite valve for delivering liquid to the mouth of an individual includes a hollow body portion and a deformable closure connected to the body portion. A plurality of spaced slits are formed in the deformable closure. A portion of the deformable closure between the slits changes shape when the bite valve is subjected to opposed compressive forces. This causes the portion of the deformable closure to change shape and the slits to open and form a plurality of openings allowing liquid flow through the deformable closure.

22 Claims, 4 Drawing Sheets

BITE VALVE HAVING A PLURALITY OF SLITS

TECHNICAL FIELD

This invention relates to a liquid delivery device for delivering water or other liquids to the mouth of an individual, for example a cyclist.

BACKGROUND ART

My U.S. Pat. No. 5,301,860, issued Apr. 12, 1994, discloses apparatus for dispensing liquid into the mouth of a cyclist. The apparatus includes a container and a delivery tube connected to the container which is held in the mouth of the cyclist.

U.S. Pat. No. 5,085,349, issued Feb. 4, 1992, discloses a system for delivering liquid from a container to a person's mouth employing a deformable valve structure in the nature of a bite valve wherein a slit in the valve is opened to permit delivery of the liquid to the person's mouth when the person bites down upon and deforms the valve.

The bite valve of U.S. Pat. No. 5,085,349 incorporates a closure member having a single slit formed therein. Deformation of the valve body by biting thereupon opens the slit only to a limited extent, the closure member walls defining the slit being forced apart essentially in a single plane to create a liquid dispensing orifice. The orifice is relatively restricted and liquid flow impeded to a considerable extent.

U.S. Pat. No. 2,219,604, issued Oct. 29, 1940, and U.S. Pat. No. 3,822,720, issued Jul. 9, 1974, disclose devices for dispensing or controlling the flow of liquid which also incorporate a single slit at the point of egress of the liquid controlled or dispensed thereby.

DISCLOSURE OF INVENTION

The present invention relates to apparatus for positioning in the mouth of an individual for selectively delivering liquid from a liquid source for consumption by the individual. The apparatus encompasses a bite valve of particular construction which provides for considerable increased liquid flow to the mouth of an individual as compared to devices such as that shown in U.S. Pat. No. 5,085,349 which employs a single slit to provide for the dispensing of liquid.

The apparatus of the present invention is formed of resilient, flexible material and includes a hollow body portion defining an interior for accommodating fluid received from a liquid source. The body portion includes a fluid inlet end communicating with the interior for receiving liquid from the liquid source and a fluid outlet end spaced from the fluid inlet end.

A deformable closure is connected to the body portion and extends across the fluid outlet end of the body portion. The closure includes an outer closure surface and an inner closure surface spaced from the outer closure surface and having a plurality of slits formed therein.

The plurality of slits are spaced from one another and extend between the outer closure surface and the inner closure surface. At least one portion of the closure is located between and defined by the plurality of slits and cooperates with the remainder of the closure to maintain the slits in closed condition to prevent liquid flow through the slits from the interior.

The at least one portion changes shape upon application of opposed external forces on the apparatus to open the plurality of slits and form a plurality of openings allowing liquid flow from the interior.

The at least one portion comprises a strip of resilient flexible material integrally connected to the remainder of the closure at opposed strip ends.

Other features, advantages, and objects of the present invention will become apparent with reference to the following description and accompanying drawings.

MODES FOR CARRYING OUT THE INVENTION

Figure 1:
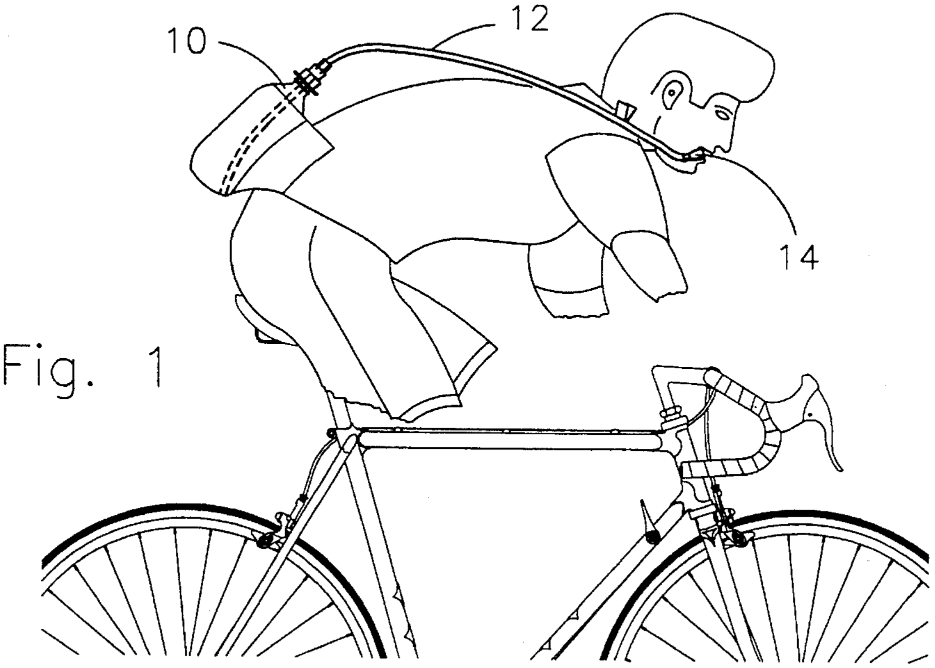
FIG. 1 is a side view of a cyclist utilizing apparatus constructed in accordance with the teachings of the present invention.

FIG. 1 illustrates apparatus constructed in accordance with the teachings of the present invention being utilized by the rider of a bicycle. A liquid container 10 is carried on the cyclist's back. A liquid delivery tube 12 projects into the container at one end thereof. The tube extends to the cyclist's mouth as shown. Attached to the end of tube 12 remote from container 10 is bite valve apparatus 14 which is employed to selectively alternately terminate or allow flow of liquid into the cyclist's mouth.

Referring now to FIGS. 2A, 2B, 2C and 2D, the bite valve apparatus 14 is shown separated from the tube. Apparatus 14 is of integral instruction and is formed of resilient, flexible material such as rubber or plastic.

Apparatus 14 includes a hollow body portion 16 defining an interior 18 for accommodating fluid received from the liquid delivery tube (the latter not shown). Body portion 16 includes a fluid inlet end 20 communicating with the interior for receiving liquid from the liquid source and a fluid outlet end 22 spaced from the fluid inlet end.

Figure 2A:
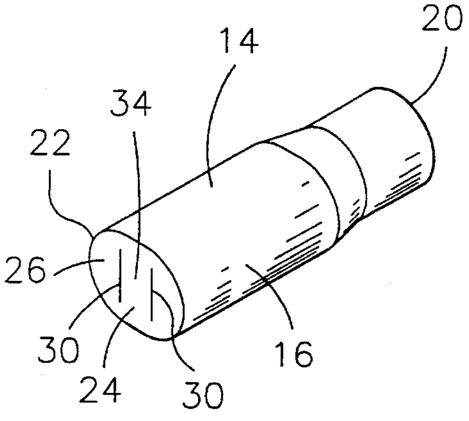
FIG. 2A is a perspective view of one form of bite valve apparatus constructed in accordance with the teachings of the present invention, the bite valve being closed.
Figure 2B:
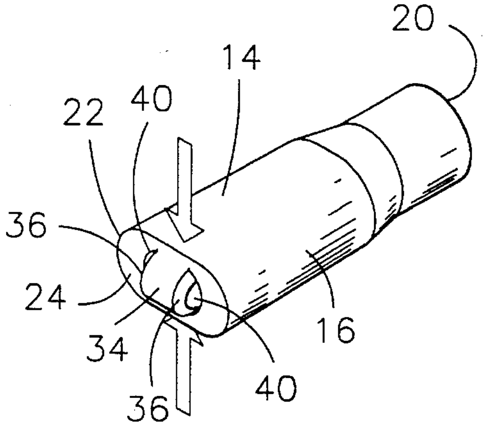
FIG. 2B is a view similar to that of FIG. 2A but illustrating in diagrammatic fashion opposed compressive forces being applied to the bite valve to open the bite valve.
Figure 2C:
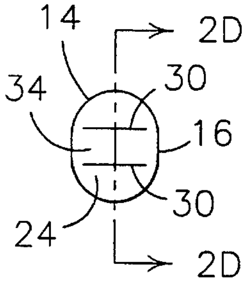
FIG. 2C is an end view of the bite valve of FIG. 2A.
Figure 2D:
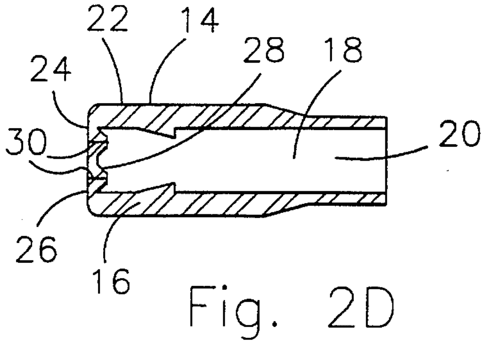
FIG. 2D is a cross-sectional view taken along the line 2D—2D of FIG. 2C.

Integrally connected to the body portion at the fluid outlet end thereof and extending across the fluid outlet end is a deformable closure 24 which normally assumes the configuration shown in FIGS. 2A, 2C, and 2D.

Closure 24 includes an outer closure surface 26 and an inner closure surface 28 spaced from the outer closure surface.

Two parallel slits 30 are formed in the closure, the slits being spaced from one another and extending between the outer closure surface and the inner closure surface.

A portion 34 of the closure is located between and defined by the slits 30 and corporates with the remainder of the closure to maintain the slits in closed condition as shown in FIGS. 2A, 2C and 2D to prevent liquid flow through the slits from the interior 18.

Portion 34 is in the form of a strip of resilient flexible material integrally connected to the remainder of the closure at opposed strip ends. When a cyclist bites down on the bite valve apparatus, opposed external forces will be applied to the apparatus as shown by the arrows in FIG. 2B. The opposed forces are generally parallel to the primary axes of the slits 30 and disposed along a first plane.

Application of the opposed forces will deform the closure 24 as shown in FIG. 2B and cause portion or strip 34 to form an outwardly projecting arch between the ends of the portion or strip. The side walls 36 of the strip are displaced outwardly relative to the remainder of the closure to form fluid outlet openings 40 at opposed sides of the strip. These openings allow a substantial flow or amount of liquid to enter the user's mouth. It will be noted that the outward movement of the strip or portion 34 is along a second plane substantially angularly disposed relative to the plane occupied by the external biting forces. In the embodiment under discussion, the second plane is generally orthogonal relative to the first plane. The closure will return to its normal position shown in FIG. 2A by removing the biting force.

FIGS. 3A through 3D illustrate an alternate form of bite valve apparatus 14A. Bite valve apparatus 14A differs from previously described bite valve apparatus 14 in that the outer closure surface is not substantially planar as is the case with bite valve apparatus 14 but includes two adjoining wall sections 44 which converge at a line of convergence 46. A slit 30 is formed in the closure 24A along the line of convergence. In addition, a slit 30 is formed in each of the wall sections. The slits 30 are substantially parallel to one another. Two portions or strips 34A are defined by the slits 30.

Figure 3A:
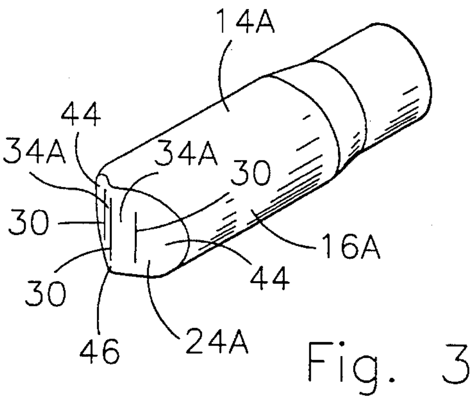
FIG. 3A is a view similar to FIG. 2A but illustrating an alternative embodiment of the bite valve.
Figure 3B:
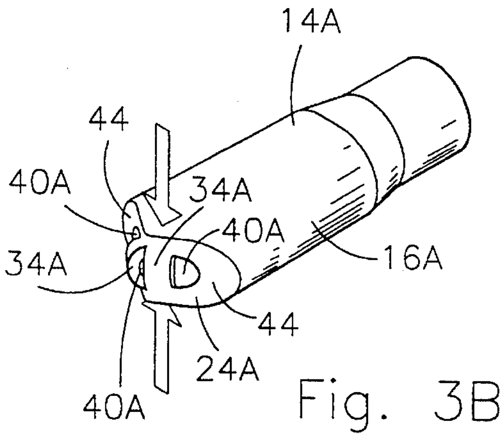
FIG. 3B is a view similar to that of FIG. 2B but illustrating the bite valve embodiment of FIG. 3A.
Figure 3C:
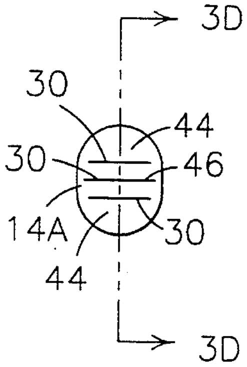
FIG. 3C is a view similar to FIG. 2C but illustrating the bite valve embodiment of FIG. 3A.
Figure 3D:
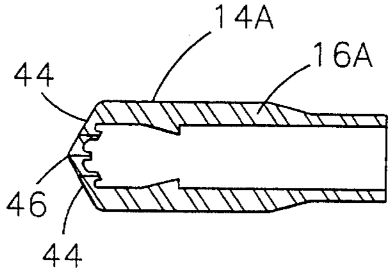
FIG. 3D is a cross-sectional view taken along the line 3D—3D of FIG. 3C.

Compressive opposed forces applied to the bite valve apparatus 14A in the direction of the slits 30 will cause both portions 34A to bulge outwardly as shown in FIG. 3B. This creates three fluid outlet openings 40A.

Referring now to FIGS. 4A through 4E, another embodiment 14B is shown. In this embodiment the outer closure surface of closure 24B is concave. The concave outer closure surface is designated by reference numeral 50. Two slits 30 are formed in closure 24B to define a strip or portion 34B. Application of opposed external compressive forces on the bite valve apparatus shown in FIG. 4B will cause the strip or portion 34B to move inwardly and be positioned within the interior of the body portion. This will result in formation of two fluid outlet openings 54.

Figure 5A:
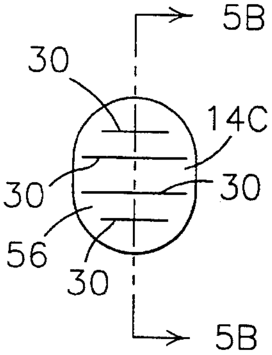
FIG. 5A is an end view of another bite valve embodiment.
Figure 5B:
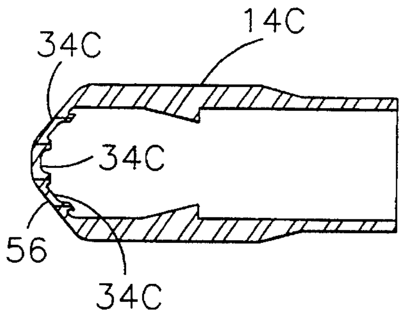
FIG. 5B is a cross-sectional view taken along the line 5B—5B in FIG. 5A.
Figure 4A:
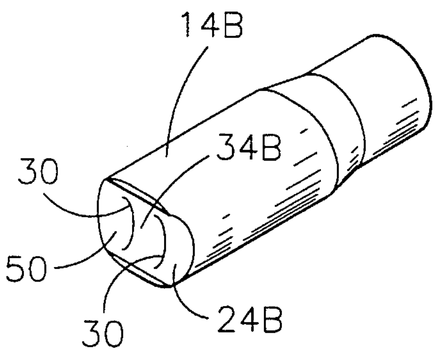
FIG. 4A is a view similar to FIG. 2A but illustrating a third embodiment of apparatus constructed in accordance with the teachings of the present invention.
Figure 4B:
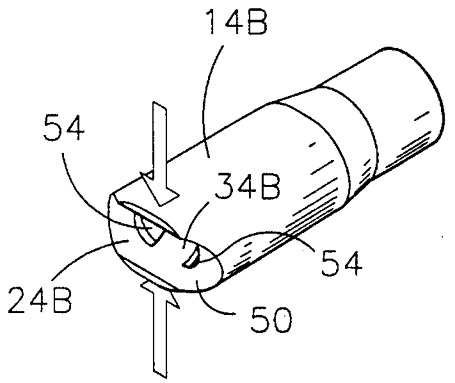
FIG. 4B is a view similar to FIG. 2B but illustrating the bite valve of FIG. 4A.
Figure 4D:
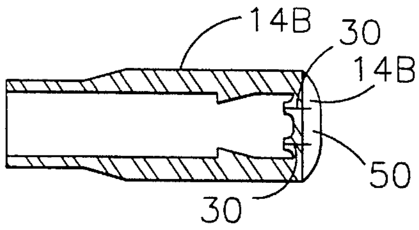
FIG. 4D is a cross-sectional view taken along the line 4D—4D of FIG. 4C.
Figure 4C:
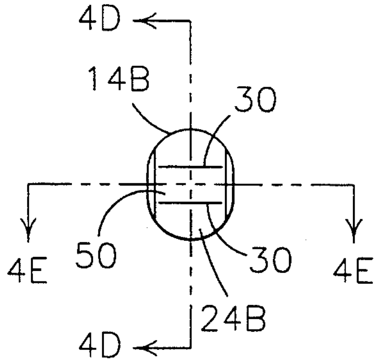
FIG. 4C is a view similar to FIG. 2C but illustrating the embodiment of FIG. 4A.
Figure 4E:
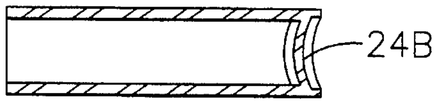
FIG. 4E is a cross-sectional view taken along the lne 4E—4E of FIG. 4C.

FIGS. 5A and 5B illustrate another embodiment of the bite valve apparatus, bite valve 14C, which employs an outwardly extending outer closure surface 56 which is generally V-shaped and somewhat blunted at the center thereof. Four slits 30 are fanned in the closure. This, of course, results in three portions or strips 34C between the slits which are deflected outwardly upon application of opposed compressive biting forces as described above with respect of the previously described other embodiments of the invention.

Figure 6A:
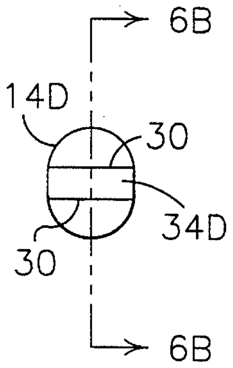
FIG. 6A is an end view of yet another embodiment of the invention.
Figure 6B:
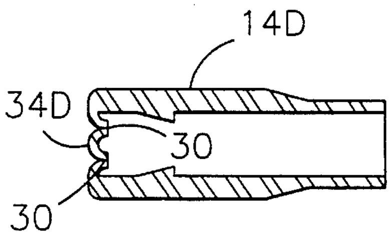
FIG. 6B is a cross-sectional view taken along the line 6B—6B in FIG. 6A.

Bite valve apparatus 14D shown in FIGS. 6A and 6B incorporates two slits 30. The strip 34D is curved along the length thereof and incorporates two curved side walls, each defining one side of a slit. Curved walls are also incorporated in the closure adjacent to the curved side walls of the strip. The curved walls of the closure are normally in engagement as shown in FIGS. 6A and 6B to prevent passage of liquid through the slits until application of opposed external forces on the apparatus along the direction of the slits. The curved walls curve inwardly and terminate in the interior of the bite valve apparatus 14D.

Figure 7B:
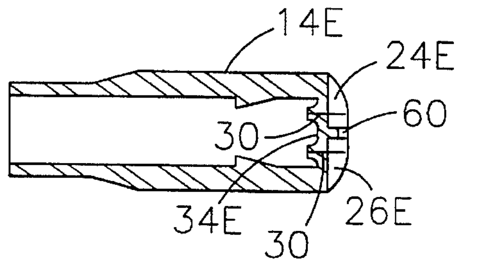
FIG. 7B is a cross-sectional view taken along the line 7B—7B of FIG. 7A.
Figure 7A:
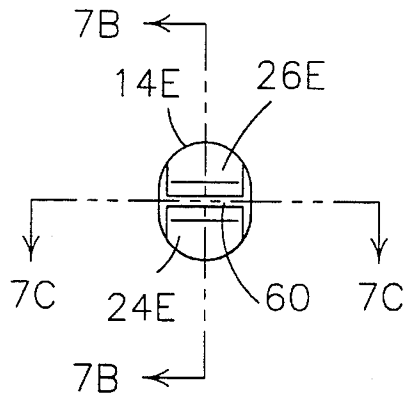
FIG. 7A is an end view of yet one more embodiment of the present invention.
Figure 7C:
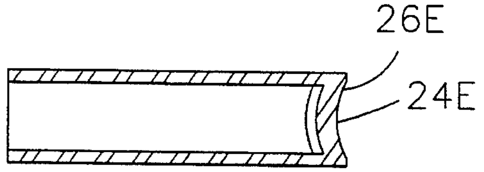
FIG. 7C is a cross-sectional view taken along the line 7C—7C of FIG. 7A.

FIGS. 7A through 7C disclose another embodiment of the invention, this embodiment being designated by reference numeral 14E. Closure 24E defines two slits 30 which are substantially parallel and spaced from one another. In this arrangement, the outer closure surface 26E is concave but has a stiffener member 60 extending across the closure to cause the strip or portion 34E to move inwardly upon application of opposed compressive biting forces on the bite valve apparatus.

Figure 8B:
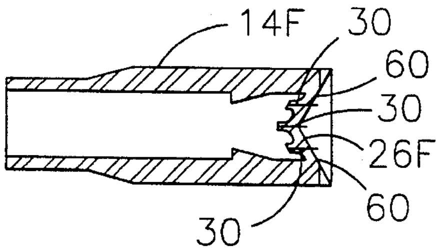
FIG. 8B is a cross-sectional view taken along the line 8B—8B of FIG. 8A.
Figure 8A:
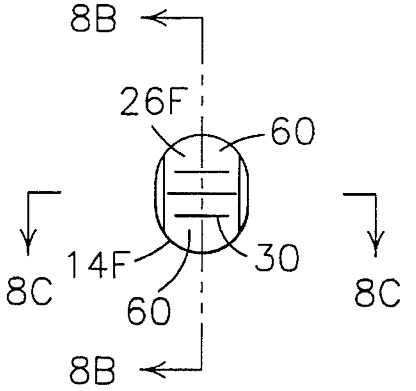
FIG. 8A is an end view of still another embodiment of the bite valve apparatus.
Figure 8C:
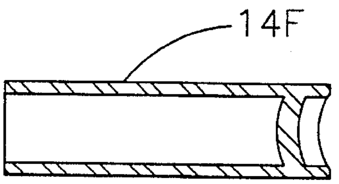
FIG. 8C is a cross-sectional view taken along the line 8C—8C in FIG. 8A.

FIGS. 8A through 8C illustrate a bite valve apparatus 14F wherein the outer closure surface 26F comprises two adjoining wall sections 60 which are substantially planar and converge inwardly to meet at a central location. Three slits 30 are formed in the closure 24F, defining two flexible portions or strips therebetween. These portions will deflect inwardly upon application of opposed externally applied compressive forces on the bite valve apparatus in the direction of the slits.

I claim:

1. Apparatus for positioning in the mouth of an individual for selectively delivering liquid from a liquid source for consummation by the individual, said apparatus being formed of resilient, flexible material, and comprising, in combination:

a hollow body portion defining an interior for accommodating fluid received from a liquid source, said body portion including a fluid inlet end communicating with said interior for receiving liquid from the liquid source and a fluid outlet end spaced from said fluid inlet end; and a deformable closure connected to said body portion and extending across the fluid outlet end of said body portion, said closure including an outer closure surface and an inner closure surface spaced from said outer closure surface and having a plurality of slits formed therein, said plurality of slits being spaced from one another and extending between said outer closure surface and said inner closure surface, and at least one portion of said closure being located between and defined by said plurality of slits and cooperating with the remainder of said closure to maintain said slits in closed condition to prevent liquid flow through said slits from said interior, said at least one portion changing shape upon application of opposed external forces on said apparatus to open said plurality of slits and form a plurality of openings allowing liquid flow from said interior.

2. The apparatus according to claim 1 wherein said at least one portion comprises a strip of resilient flexible material integrally connected to the remainder of said closure at opposed strip ends.

3. The apparatus according to claim 2 wherein said strip of resilient flexible material includes spaced side walls, said strip of resilient flexible material deflecting outwardly relative to the remainder of said closure upon application of opposed external forces on said apparatus to form an outwardly projecting arch between said opposed strip ends, and said spaced side walls of said strip being displaced outwardly relative to the remainder of said closure to form fluid outlet openings at opposed sides of said strip of resilient flexible material.

4. The apparatus according to claim 2 wherein said strip of resilient flexible material includes spaced side walls, said strip of resilient flexible material deflecting inwardly relative to the remainder of the closure upon application of opposed external forces on said apparatus to form an inwardly projecting arch between said opposed strip ends, and said spaced side walls being displaced inwardly relative to the remainder of said closure and into said interior to form fluid outlet openings at opposed sides of said strip of resilient flexible material.

5. The apparatus according to claim 2 wherein said strip of resilient flexible material has a curved cross section.

6. The apparatus according to claim 2 additionally comprising stiffener means attached to and extending along said strip of resilient flexible material.

7. The apparatus according to claim 2 wherein said closure includes a plurality of curved flexible walls defining said slits, at least two of said curved walls comprising curved side walls of said strip and at least two of said curved walls formed on said closure adjacent to the curved side walls of said strip, said curved walls being in engagement to prevent passage of liquid through said slits until application of opposed external forces on said apparatus.

8. The apparatus according to claim 7 wherein said curved walls curve inwardly and terminate in said interior.

9. The apparatus according to claim 1 wherein said outer closure surface is convex.

10. The apparatus according to claim 1 wherein said outer closure surface is concave.

11. The apparatus according to claim 1 wherein at least some of said plurality of slits are generally parallel to one another.

12. The apparatus according to claim 1 wherein said outer closure surface is substantially planar.

13. The apparatus according to claim 1 wherein said outer closure surface includes two adjoining wall sections which converge at a line of convergence, one of said slits being located substantially along said line of convergence.

14. The apparatus according to claim 13 wherein at least one slit is located in each of said wall sections, said slits located in each of said wall sections being generally parallel to each other and to the slit located along said line of convergence.

15. The apparatus according to claim 13 wherein said wall sections are substantially planar and converge in an outward direction.

16. The apparatus according to claim 13 wherein said wall sections are substantially planar and converge in an inward direction.

17. The apparatus according to claim 1 wherein said body portion and said closure are of integral construction.

18. The apparatus according to claim 1 wherein said body portion is generally tubular shaped.

19. In combination:

a container for containing liquid;

a liquid delivery tube leading from said container; and bite valve apparatus connected to said liquid delivery tube for positioning in the mouth of an individual for selectively delivering liquid from said container for consummation by the individual, said bite valve apparatus being formed of resilient, flexible material, and comprising:

a hollow body portion defining an interior for accommodating fluid received from said container through said delivery tube, said body portion including a fluid inlet end communicating with said interior connected to said delivery tube for receiving liquid from the container and a fluid outlet end spaced from said fluid inlet end; and a deformable closure connected to said body portion and extending across the fluid outlet end of said body portion, said closure including an outer closure surface and an inner closure surface spaced from said outer closure surface and having a plurality of slits formed therein, said plurality of slits being spaced from one another and extending between said outer closure surface and said inner closure surface, and at least one portion of said closure being located between and defined by said plurality of slits and cooperating with the remainder of said closure to maintain said slits in closed condition to prevent liquid flow through said slits from said interior, said at least one portion changing shape upon application of opposed external forces on said bite valve apparatus to open said plurality of slits and form a plurality of openings allowing liquid flow from said interior.

20. Bite valve apparatus for positioning in the mouth of an individual for selectively delivering liquid from a liquid source for consummation by the individual, said bite valve apparatus being of unitary construction, and formed of resilient, flexible material, said bite valve apparatus comprising, in combination:

a hollow body portion defining an interior for accommodating fluid received from a liquid source, said body portion including a fluid inlet end communicating with said interior for receiving liquid from the liquid source and a fluid outlet end spaced from said fluid inlet end; and a deformable closure connected to said body portion and extending across the fluid outlet end of said body portion, said closure including an outer closure surface and an inner closure surface spaced from said outer closure surface and having a plurality of slits formed therein, said plurality of slits being spaced from one another and extending between said outer closure surface and said inner closure surface, and at least one portion of said closure being located between and defined by said plurality of slits and cooperating with the remainder of said closure to maintain said slits in closed condition to prevent liquid flow through said slits from said interior, said at least one portion upon application of opposed biting forces on said bite valve apparatus along a first plane moving in a second plane angularly disposed relative to said first plane to open said plurality of slits and form openings allowing liquid flow from said interior.

21. Apparatus for selectively delivering liquid from a liquid source, said apparatus comprising, in combination:

a hollow body portion defining an interior for accommodating fluid received from a liquid source, said body portion including a fluid inlet communicating with said interior for receiving liquid from the liquid source and a fluid outlet spaced from said fluid inlet; and a deformable closure formed of resilient, flexible material connected to said body portion and extending across the fluid outlet of said body portion, said closure including a first closure surface and a second closure surface spaced from said first closure surface and having a plurality of slits formed therein, said plurality of slits being spaced from one another and extending between said first closure surface and said second closure wall, and at least one portion of said closure being located between and defined by said plurality of slits and cooperating with the remainder of said closure to maintain said slits in closed condition to prevent liquid flow through said slits from said interior, said at least one portion changing shape upon application of forces on said apparatus to open said plurality of slits and form a plurality of openings allowing liquid flow from said interior.

22. The apparatus according to claim 21 wherein said plurality of slits are defined by spaced closure segments of increased thickness, said portion changing shape responsive to an increase of liquid pressure at one of said closure surfaces.

* * * * *